United States Patent
Hu et al.

(10) Patent No.: US 10,022,181 B2
(45) Date of Patent: Jul. 17, 2018

(54) THERMOCOUPLE MESH SYSTEM FOR A MEDICAL DEVICE

(75) Inventors: Yixin Hu, Montréal (CA); Wlodzimierz Sadzynski, Chateauguay (CA); Melita A. Tabao, Montréal (CA); Teresa Mihalik, Montréal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 3182 days.

(21) Appl. No.: 11/527,881

(22) Filed: Sep. 27, 2006

(65) Prior Publication Data

US 2008/0097421 A1  Apr. 24, 2008

(51) Int. Cl.
| | |
|---|---|
| *A61B 18/22* | (2006.01) |
| *A61B 18/14* | (2006.01) |
| *A61B 17/00* | (2006.01) |
| *A61B 18/00* | (2006.01) |
| *A61B 18/02* | (2006.01) |
| *A61B 18/04* | (2006.01) |
| *A61F 7/00* | (2006.01) |

(52) U.S. Cl.
CPC ............... *A61B 18/1492* (2013.01); *A61B 2017/00101* (2013.01); *A61B 2018/0022* (2013.01);
(Continued)

(58) Field of Classification Search
CPC ...... A61B 18/1492; A61B 2017/00101; A61B 2018/00023; A61B 2018/00214; A61B 2018/00797; A61B 2018/00821; A61B 2018/0212; A61B 2018/046; A61B 2018/0022; A61B 2017/00022; A61B 2017/00092; A61B 2017/00199;
(Continued)

(56) References Cited

U.S. PATENT DOCUMENTS

| | | | |
|---|---|---|---|
| 4,776,334 | A | 10/1988 | Prionas |
| 5,776,129 | A | 7/1998 | Mersch |

(Continued)

FOREIGN PATENT DOCUMENTS

| | | |
|---|---|---|
| RU | 2165695 C2 | 4/2001 |
| WO | 0117451 A1 | 3/2001 |

(Continued)

OTHER PUBLICATIONS

Supplementary European Search Report, Nov. 23, 2011 for Application No. EP 07 71 9990, 5 pages.

(Continued)

*Primary Examiner* — David Shay
(74) *Attorney, Agent, or Firm* — Christopher & Weisberg, P.A.

(57) ABSTRACT

The present invention includes a medical device providing for the measurement and/or monitoring of the thermal conditions and/or environment existing across a substantial portion of a thermal element disposed on the medical device and the corresponding tissue region being treated by the device. The medical device of the present invention may generally include an elongate body having a thermal element coupled thereto for providing thermal energy to a desired tissue region, as well as a thermocouple array providing a plurality of temperature measurement positions about the thermal element. The thermocouple array may include one or more thermocouple elements arranged as a mesh or wire structure disposed about a substantial portion of the surface area of the thermal element.

12 Claims, 3 Drawing Sheets

(52) U.S. Cl.
CPC ............... *A61B 2018/00023* (2013.01); *A61B 2018/00214* (2013.01); *A61B 2018/00797* (2013.01); *A61B 2018/00821* (2013.01); *A61B 2018/0212* (2013.01); *A61B 2018/046* (2013.01); *A61F 2007/0054* (2013.01)

(58) Field of Classification Search
CPC ........... A61B 2017/00256; A61B 2017/00292; A61B 2018/00101; A61B 2018/00375; A61B 2018/00642; A61B 2018/0262; A61F 2007/0054; A61F 7/12; A61F 7/123; A61F 2007/0056; A61F 2007/0058; A61F 2007/0091; A61F 2007/0095; A61F 2007/126
USPC .................................. 606/10–13, 34, 41–47
See application file for complete search history.

(56) References Cited

U.S. PATENT DOCUMENTS

| | | | |
|---|---|---|---|
| 5,891,136 A | 4/1999 | McGee et al. | |
| 6,428,536 B2* | 8/2002 | Panescu et al. | 606/34 |
| 6,575,966 B2 | 6/2003 | Lane et al. | |
| 6,640,120 B1* | 10/2003 | Swanson | A61B 18/1492 607/101 |
| 6,837,886 B2* | 1/2005 | Collins et al. | 606/47 |
| 7,097,643 B2 | 8/2006 | Cornelius et al. | |
| 2003/0153905 A1 | 8/2003 | Edwards et al. | |
| 2004/0147852 A1 | 7/2004 | Brister et al. | |
| 2006/0115221 A1 | 6/2006 | Chalifoux et al. | |

FOREIGN PATENT DOCUMENTS

| | | | | |
|---|---|---|---|---|
| WO | 2004087249 A2 | 10/2004 | | |
| WO | WO 2004/087249 | * 10/2004 | ......... | A61B 18/1492 |
| WO | 2006058251 A2 | 6/2006 | | |

OTHER PUBLICATIONS

International Search Report and Written Opinion dated Oct. 26, 2007, for corresponding International Application No. PCT/CA2007/001074; International Filing Date: Jun. 19, 2007 consisting of 12 pages.

* cited by examiner

THERMOCOUPLE MESH SYSTEM FOR A MEDICAL DEVICE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to surgical devices, and more particularly to minimally invasive surgical systems for thermally affecting a tissue region.

BACKGROUND OF THE INVENTION

Many surgical procedures involve thermally affecting tissue, including those in which a catheter is placed inside the body for ablating or otherwise treating a desired tissue region. For example, a catheter having a thermally transmissive region for directing thermal energy may be selected for treating cardiac tissue in the treatment of an arrhythmia, whereby a lesion or other non-electrically conductive region is formed. During such a procedure, it is important for an operating physician to ascertain and/or monitor the temperature of the ablative energy being applied to the tissue, as to ensure that the appropriate temperature levels are reached, which correspond to an effective ablation treatment. While existing devices may include a temperature sensor or other thermal monitoring component disposed somewhere on a catheter for providing an assessment of the temperature of the device and/or the tissue being affected, the measured information obtained may be incomplete or misleading, as typically sensors are either inside a portion of the device or only cover a small portion of the exterior actually contacting the tissue.

As such, if a device provides thermal energy across a relatively large tissue site, monitoring the temperature at a single site or measuring an average temperature of a portion of the device does not provide a complete assessment of the thermal environment present between the device and the tissue being affected. The lack of this needed information could result in gaps or inconsistencies across the treated tissue region, and, more seriously, could lead to unintended thermal damage occurring in sensitive tissue regions, such as the heart.

In view of the above-mentioned limitations, it would be desirable to provide for the measurement and/or monitoring of the thermal conditions and/or environment existing across a substantial portion of a thermal device and the corresponding tissue region being treated by the device.

SUMMARY OF THE INVENTION

The present invention advantageously provides for the measurement and/or monitoring of the thermal conditions and/or environment existing across a substantial portion of a thermal element disposed on the medical device and the corresponding tissue region being treated by the device. The medical device of the present invention may generally include an elongate body having a thermal element coupled thereto for providing thermal energy to a desired tissue region, where the thermal element may include an expandable element or other receptacle for receiving a coolant therein. The elongate body of the medical device may include one or more lumens for fluid flow therethrough, including an injection lumen, an exhaust lumen, and/or a guidewire lumen.

The medical device of the present invention may further include a thermocouple array providing a plurality of temperature measurement positions about the thermal element, where the thermocouple array may include one or more thermocouple elements arranged as a mesh or wire structure disposed about a substantial portion of the surface area of the thermal element. The thermocouple array may include one or more insulated thermocouple segments, where portions of the insulation are removed at desired locations for providing a temperature measurement at that particular position. A console may further be provided in communication with the medical device and the thermocouple array for monitoring and/or controlling the operation of the medical device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
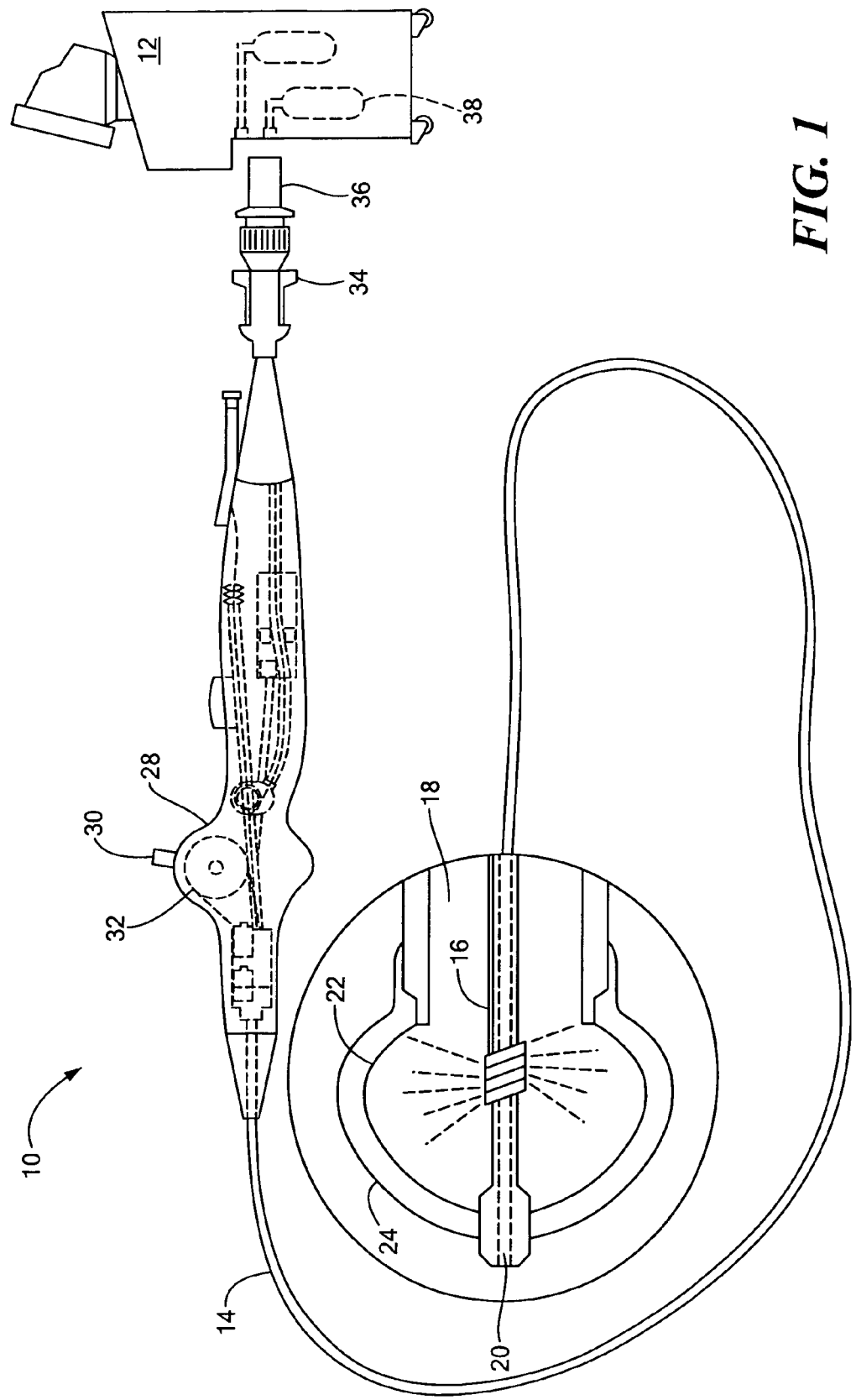
FIG. 1 illustrates an embodiment of a medical device in accordance with the present invention.

Referring now to FIG. 1, an exemplary system including is illustrated for minimally invasive surgery. The system may include a console 12 and a medical device 10, such as a multi-lumen catheter having an elongate body 14. The elongate body 14 may define a proximal portion and a distal portion, and may further include one or more lumens disposed within the elongate body 14 thereby providing mechanical, electrical, and/or fluid communication between the proximal portion of the elongate body 14 and the distal portion of the elongate body 14. For example, the elongate body 14 may include an injection lumen 16 and an exhaust lumen 18 defining a fluid flow path therethrough.

In addition, the elongate body 14 may include a guidewire lumen 20 extending along at least a portion of the length of the elongate body 14 for over-the-wire applications, where the guidewire lumen 20 may define a proximal end and a distal end. The guidewire lumen 20 may be movably disposed within at least a portion of the elongate body 14 such that the distal end of the guidewire lumen 20 extends beyond the and out of the distal portion of the elongate body 14.

The medical device 10 of the present invention may further include a thermal element for providing thermal energy to a desired tissue region, such as an expandable element 22 at least partially disposed on the elongate catheter body, a fixed-volume body or other fluid receptacle, an RF electrode (not shown), or the like. The expandable element 22 may include a balloon or other expandable structure, which may define a proximal end coupled to the distal portion of the elongate body 14 of the catheter, while further defining a distal end coupled to the tip portion and/or the distal end of the guidewire lumen 20. In addition, the expandable element 22 may have any of a myriad of shapes, and may further include one or more material layers providing for puncture resistance, radiopacity, or the like. The expandable element 22 may be in communication with the fluid injection and exhaust lumens of the medical device 10 as described above, i.e., a fluid flow path may provide an inflation fluid, such as a cryogenic fluid or the like, to the interior of the expandable element 22.

Figure 2:
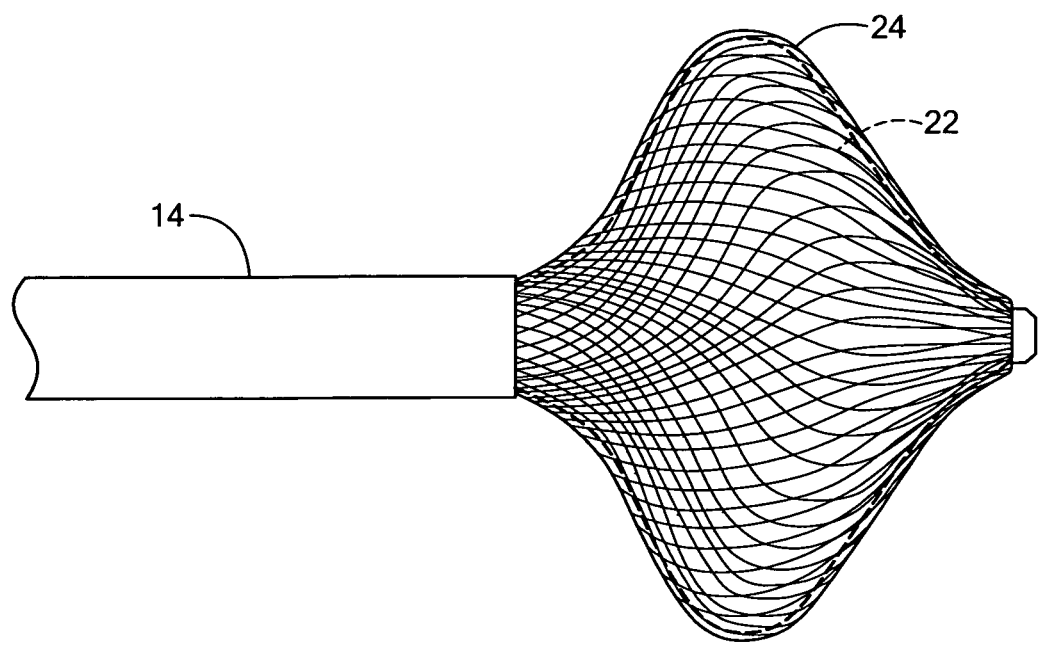
FIG. 2 depicts an embodiment of a medical device in accordance with the present invention.
Figure 3:
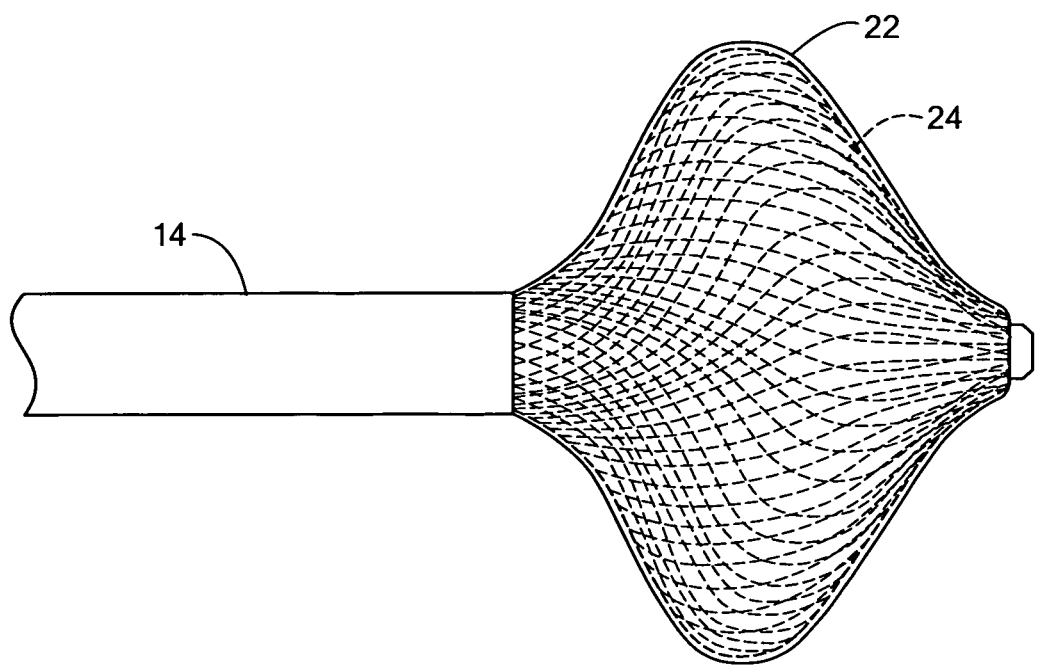
FIG. 3 shows an embodiment of a medical device in accordance with the present invention.
Figure 4:
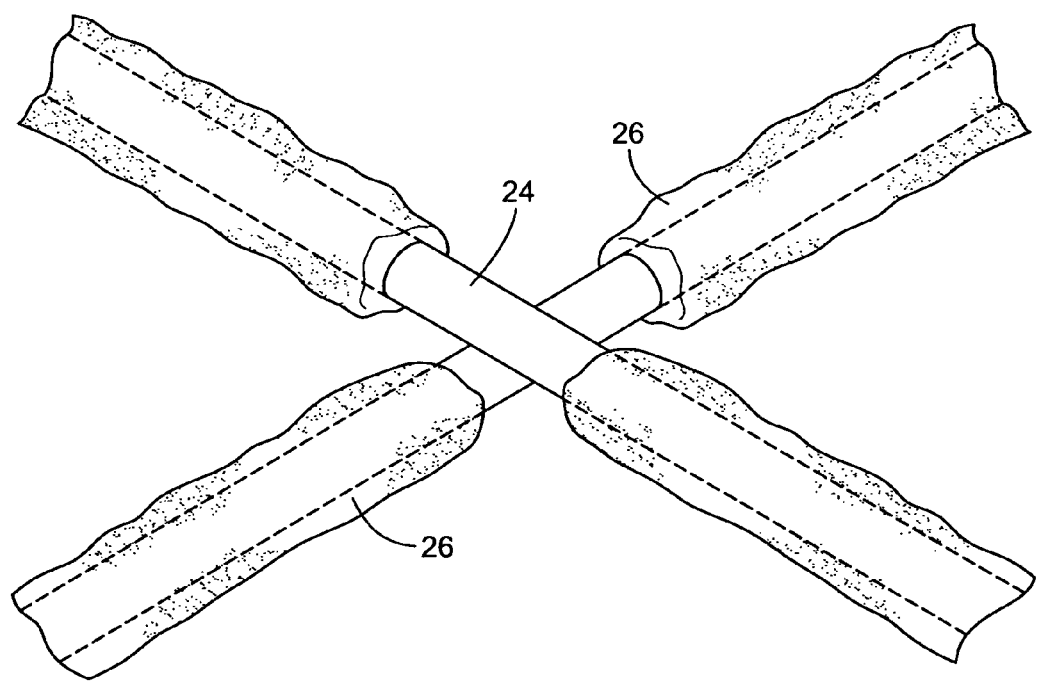
FIG. 4 illustrates an embodiment of a medical device in accordance with the present invention.

Now referring to FIGS. 2-4, the medical device 10 of the present invention may further include a thermocouple array providing a plurality of temperature measurement positions about the expandable element on the distal portion of the elongate body 14. The thermocouple array may include one or more thermocouple elements 24 arranged as a mesh or wire structure, which may further be configurable into a plurality of geometric configurations, shapes, and or dimensions. In addition, the thermocouple array may be biased towards a particular shape or geometric configuration to effect treatment toward a desired tissue region. As used herein, the term "mesh" is intended to include any element having an openwork fabric or structure, and may include but is not limited to, an interconnected network of wire-like segments, a sheet of material having numerous apertures and/or portions of material removed, or the like. In addition to providing a plurality of temperature measurement positions, the mesh configuration may provide increased structural integrity and strength to resist breaking and/or kinking of the thermocouple array.

The one or more thermocouple elements 24 of the thermocouple array may include an insulation 26 covering at least a portion of the thermocouple elements 24, where portions of the insulation are removed at desired locations for providing a temperature measurement at that particular position. In addition, the thermocouple array may be at least partially disposed on either an interior or exterior portion of the expandable element 22. Should the medical device 10 include multiple expandable elements or an expandable element 22 having multiple layers, the thermocouple array may be positioned and/or integrated between the multiple expandable elements or layers. Where the thermocouple array is not directly exposed to or otherwise able to contact the tissue being treated, the thermal properties of an intervening material layer may be used to extrapolate or otherwise calculate the actual thermal characteristics of the surface of the medical device and/or the tissue given the measurements or indications provided by the thermocouple array. The thermocouple array may be situated about the expandable element 22 of the medical device such that the plurality of temperature measurement positions extends across a significant portion of the surface area of the expandable element 22 or thermal element, thereby providing numerous reference points for monitoring and/or controlling the thermal characteristics of the medical device when in contact with and/or thermally affecting a tissue region.

Again referring to FIG. 1, the catheter body of the medical device 10 may have a proximal end that is mated to a handle 28, where the handle may include an element such as a lever or knob 30 for manipulating the catheter body and/or additional components of the medical device 10. For example, a pull wire with a proximal end and a distal end may have its distal end anchored to the elongate body 14 at or near the distal end. The proximal end of the pull wire may be anchored to an element such as a cam 32 in communication with and responsive to the lever 30. The handle 28 can further include circuitry for identification and/or use in controlling of the ablation catheter or another component of the system.

The handle 28 may also include connectors that are matable directly to a fluid supply/exhaust and control unit or indirectly by way of one or more umbilicals for providing fluid communication with the elongate body 14. In the system illustrated, the handle 28 is provided with a first connector 34 that is matable with a co-axial fluid umbilical (not shown) and a second connector 36 that is matable with an electrical umbilical (not shown) that can further include an accessory box (not shown). The first and second connectors may provide fluid, mechanical, and/or electrical communication between portions of the medical device 10 and the console 12, including providing communication between the console 12 and the thermocouple array of the medical device 10.

The console 12 may house electronics and software for monitoring, controlling and/or recording the characteristics of surgical procedure, including but not limited to the particular thermal environment as indicated by the thermocouple array. The console may further control delivery of a liquid refrigerant under high pressure from a reservoir 38, through an umbilical, to the elongate body and/or the expandable element. The console 12 can also include an apparatus for recovery of expanded refrigerant vapor from the medical device 10 and recompression of the vapor.

In an exemplary use of a system including the medical device 10 of the present invention, the medical device 10 may be positioned in proximity to a tissue region for application of thermal energy thereto. Once the desired positioning has been achieved, the application of thermal energy via the medical device 10 may begin. The thermal energy may include providing a coolant flow through the medical device 10 to the expandable element 22 to impart cryogenically ablative temperatures to the tissue, or may alternatively include a heating element such as an RF electrode or the like for effectively heating the tissue to the desired temperature. Irrespective of the thermal modality in use, the thermocouple array may provide an indication of the thermal characteristics existing on the surface of the tissue region, on the surface of the medical device, and/or the region in between, if any. The information provided by the thermocouple array may be communicated to the console and provided to an operating physician. The particular measurements provided by the thermocouple array may be individualized, i.e., a particular measured value may be provided for each temperature measurement point of the thermocouple array, with the information being provided to a physician in an appropriate format, such as a graphical indication of the temperature across the surface of the medical device 10 or the like. As the thermocouple array may be disposed about a substantial portion of the surface area of the thermal element, a more complete, accurate, and enhanced assessment is available of the thermal interaction between the medical device and the tissue being treated. Accordingly, modifications in the particular amount of thermal energy being provided and/or the positioning of the medical device may be modified in view of the information provided by the thermocouple array, leading to improved operation and treatment results.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an expandable thermal element for providing thermal energy; and
   a thermocouple array arranged as a mesh of interwoven wire-like segments disposed about the expandable thermal element, and wherein each of the interwoven wire-like segments of the thermocouple array includes a thermally insulated portion and a thermally uninsulated portion, adjacent thermally uninsulated portions being in contact with each other.

2. The medical device according to claim 1, wherein the expandable thermal element includes a balloon.

3. The medical device according to claim 1, further comprising a console in communication with the thermocouple array.

4. The medical device according to claim 1, wherein the expandable thermal element is coupled to an elongate body, the elongate body defining a fluid flow path therethrough in fluid communication with the expandable element.

5. The medical device according to claim 1, wherein the expandable thermal element includes an interior surface and an exterior surface, the thermocouple array being disposed on the exterior surface of the expandable thermal element.

6. The medical device according to claim 1, wherein the expandable thermal element includes an interior surface and an exterior surface, the thermocouple array being disposed on the interior surface of the expandable thermal element.

7. A medical device, comprising:
   an elongate body defining a fluid flow path therethrough;
   an expandable element coupled to the elongate body and in fluid communication with the fluid flow path, the expandable element having an interior portion and an exterior portion; and
   a thermocouple array disposed on the exterior portion of the expandable element, wherein the thermocouple array includes a mesh of interwoven segments, each of the segments of the thermocouple array including thermally insulated portions and thermally uninsulated portions, adjacent thermally uninsulated portions being in contact with each other.

8. The medical device according to claim 7, wherein the thermocouple array is disposed on an exterior surface of the expandable element.

9. The medical device according to claim 7, wherein the thermocouple array is disposed on an interior surface of the expandable element.

10. The medical device according to claim 7, further comprising a console coupled to the elongate body and in communication with the thermocouple array.

11. The medical device according to claim 10, wherein the console includes a coolant reservoir in fluid communication with the expandable element.

12. A cryogenic device, comprising:
    an elongate body defining a fluid flow path therethrough;
    an expandable element coupled to the elongate body and in fluid communication with the fluid flow path, the expandable element having an interior portion and an exterior portion;
    a thermocouple array disposed on the exterior portion of the expandable element, wherein the thermocouple array includes an interwoven mesh, the thermocouple array including at least one thermally insulated portion and at least one thermally uninsulated portion, adjacent thermally uninsulated portions being in contact with each other; and
    a console coupled to the elongate body, wherein the console includes a reservoir of coolant in fluid communication with the expandable element.

* * * * *